United States Patent [19]
Noren

[11] Patent Number: 5,331,844
[45] Date of Patent: Jul. 26, 1994

[54] METHOD AND DEVICE FOR MEASURING THE VISCOSITY OF A FLOWING FLUID

[76] Inventor: Anders Noren, Fafnervagen 30, Djursholm, S-182 65, Sweden

[21] Appl. No.: 82,552

[22] Filed: Jun. 28, 1993

Related U.S. Application Data

[63] Continuation-in-part of Ser. No. 689,841, May 23, 1991, abandoned.

[30] Foreign Application Priority Data

Dec. 1, 1988 [SE] Sweden .............................. 8804354-2

[51] Int. Cl.$^5$ .............................................. G01N 11/00
[52] U.S. Cl. ..................................... 73/54.33; 73/54.31
[58] Field of Search ............... 73/54.28, 54.32, 54.33, 73/54.34, 54.35

[56] References Cited

U.S. PATENT DOCUMENTS

| | | | |
|---|---|---|---|
| 1,911,267 | 5/1933 | Danks | 73/861.88 |
| 2,076,816 | 4/1937 | Hess | 73/59 |
| 2,267,317 | 12/1941 | Veenschoten | 73/59 |
| 2,354,299 | 7/1944 | Bays | 73/59 |
| 3,285,058 | 11/1966 | Ostroot | 73/54.28 |
| 3,426,595 | 2/1969 | Skelton | 73/861.81 |
| 3,465,574 | 9/1969 | Ezekiel et al. | 73/54.32 |
| 3,572,086 | 3/1971 | Johnston | 73/54.32 |
| 3,710,622 | 1/1973 | Hammond et al. | 73/861.84 |
| 4,377,091 | 3/1983 | DeCarlo et al. | 73/861.87 |
| 4,773,253 | 9/1988 | Francisco, Jr. | 73/32 R |

FOREIGN PATENT DOCUMENTS

| | | | |
|---|---|---|---|
| 0363019 | 12/1972 | U.S.S.R. | 73/54.35 |
| 1278678 | 12/1986 | U.S.S.R. | 73/54.35 |

*Primary Examiner*—Richard E. Chilcot, Jr.
*Assistant Examiner*—R. Biegel
*Attorney, Agent, or Firm*—Larson and Taylor

[57] ABSTRACT

A device for measuring the viscosity of the fluid flowing in a closed passage includes a rotor whose speed of rotation is directly dependent on the rate of flow of the fluid. The rotor is connected to an activatable and deactivatable brake means which has an adjustable braking force. Depending on the setting of the brake means, the brake is operative to cause a greater or smaller lag in the rotary speed of the rotor in relation to an unbraked rotor or a rotor braked with a smaller force. The measuring means is operative to determine the resultant different rotational speeds of the rotor and the different in these speeds is a measurement of viscosity.

11 Claims, 4 Drawing Sheets

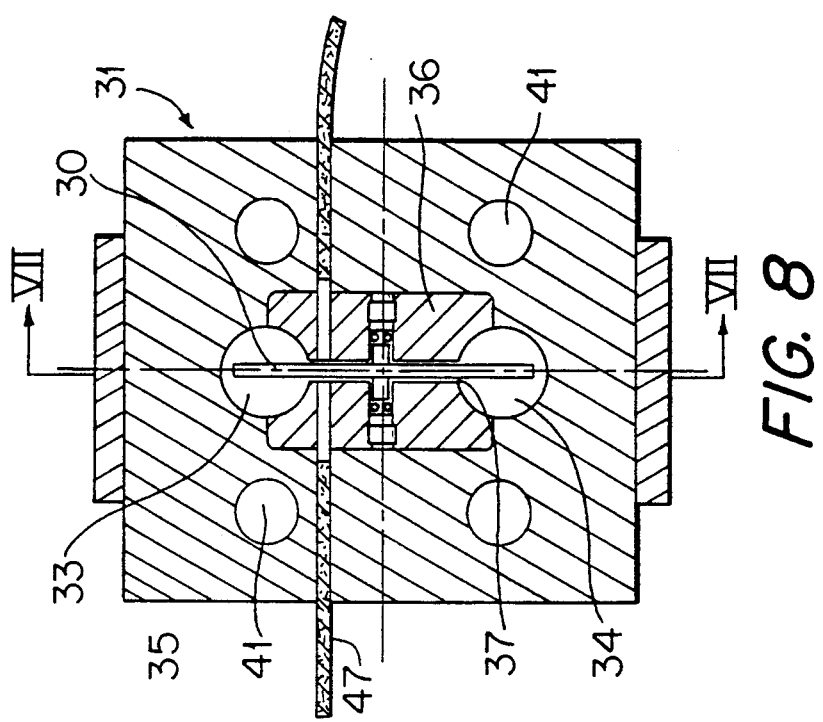
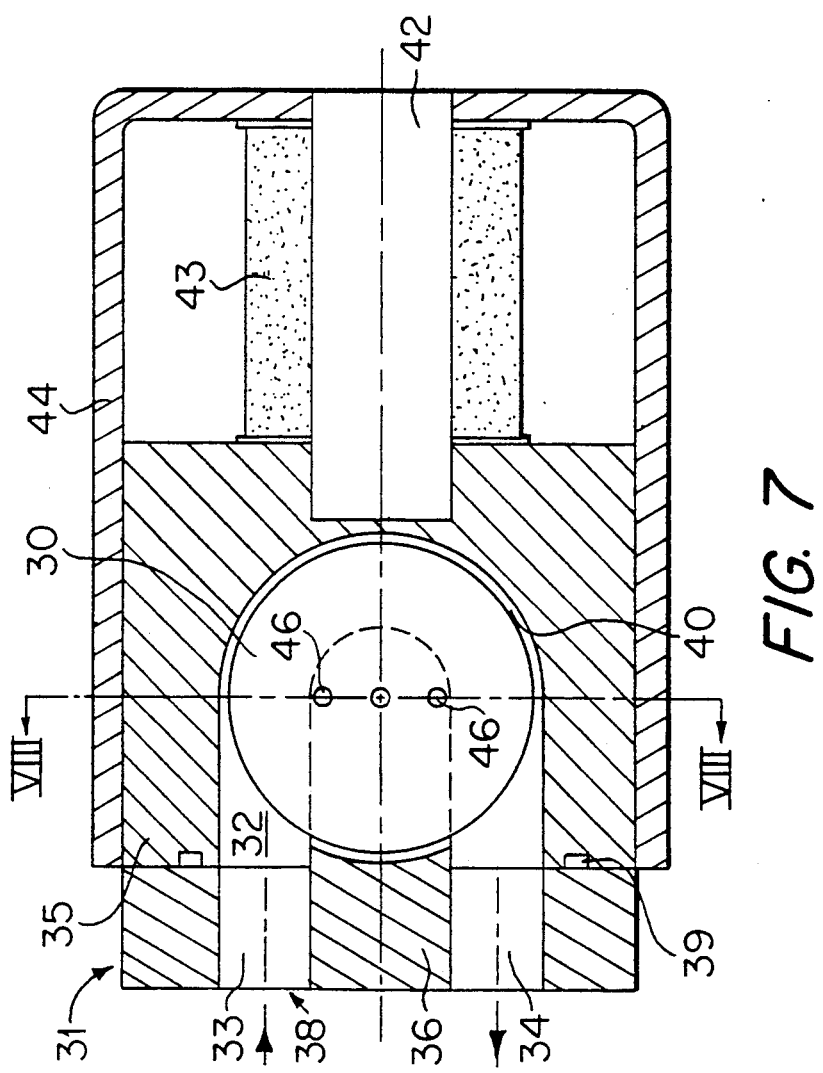
FIG. 7
FIG. 8

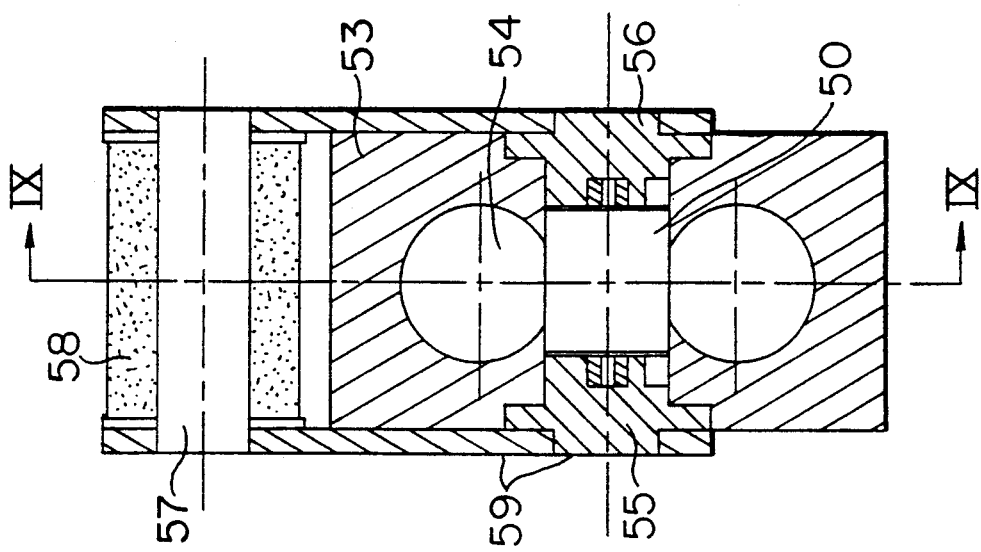
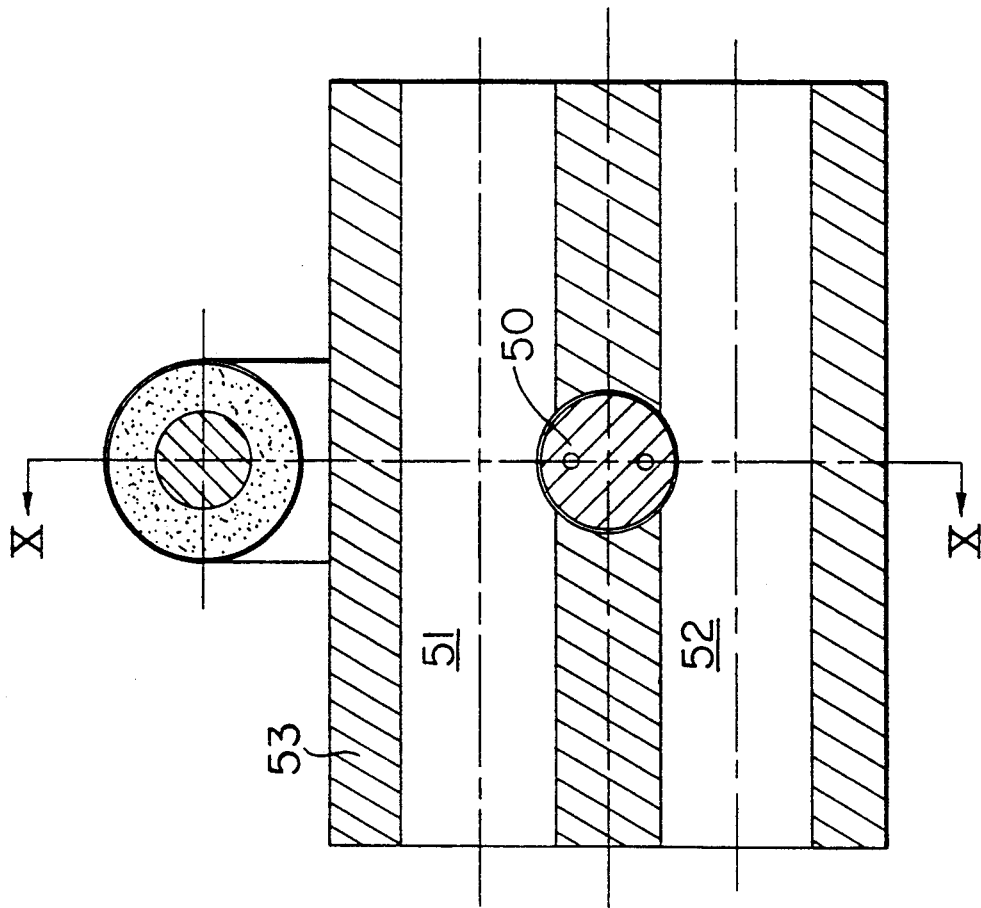
FIG. 10
FIG. 9

METHOD AND DEVICE FOR MEASURING THE VISCOSITY OF A FLOWING FLUID

This application is a continuation-in-part of co-pending U.S. patent application Ser. No. 07/689,841, filed May 23, 1991, now abandoned.

The present invention relates to a method and to a device for measuring the viscosity of a fluid flowing in a closed passage, the device comprising a rotor which is surrounded by the fluid and the speed of rotation of which is directly dependent on the flow rate of the fluid passing through the passage.

The object of the present invention is to provide a novel method and a novel device for measuring the viscosity of a fluid flowing in a closed passage such as to enable such measurements to be made in a simpler fashion that has hitherto been possible. The invention is characterized in that the rotor is driven directly by the fluid and in that there is connected to the rotor a braking device which can be activated and deactivated and the braking force of which can be adjusted so that according to the braking force applied, the rotor will rotate at a slower speed, to a greater or lesser extent, in relation to an unbraked rotor or to a rotor which has been braked with a smaller braking force; and in that measuring means are provided for determining the resultant different speeds of rotation of the rotor, this difference in rotor speeds being a measurement of the viscosity of the fluid.

In the case of one preferred embodiment of the inventive measuring device, the rotor is carried symmetrically by a shaft which extends substantially at right angles to the longitudinal axis of the fluid passage and the rotor shaft is positioned asymmetrically in relation to the longitudinal axis of said passage, and in which device the measuring means operative to determine the rotational speed of the rotor comprises at least one bore in the rotor which extends parallel with the rotor shaft and through which light is conducted from a light source arranged on one side of the rotor to a light-receiver arranged on the other side of the rotor. In a preferred embodiment, the braking device comprises an electromagnetic brake having a coil and magnetic poles.

The invention will now be described in more detail with reference to the accompanying drawings in which:

FIG. 7 is a longitudinal section view of a third embodiment of a viscosity measuring device of the invention taken along line VII—VII of FIG. 8;

FIG. 8 is a cross-sectional view taken along line VIII—VIII of FIG. 7;

FIG. 9 is a longitudinal section view of a fourth embodiment of a viscosity measuring device of the invention taken along line IX—IX of FIG. 10; and FIG. 10 is a cross-sectional view taken along line X—X of FIG. 9.

Figure 2:
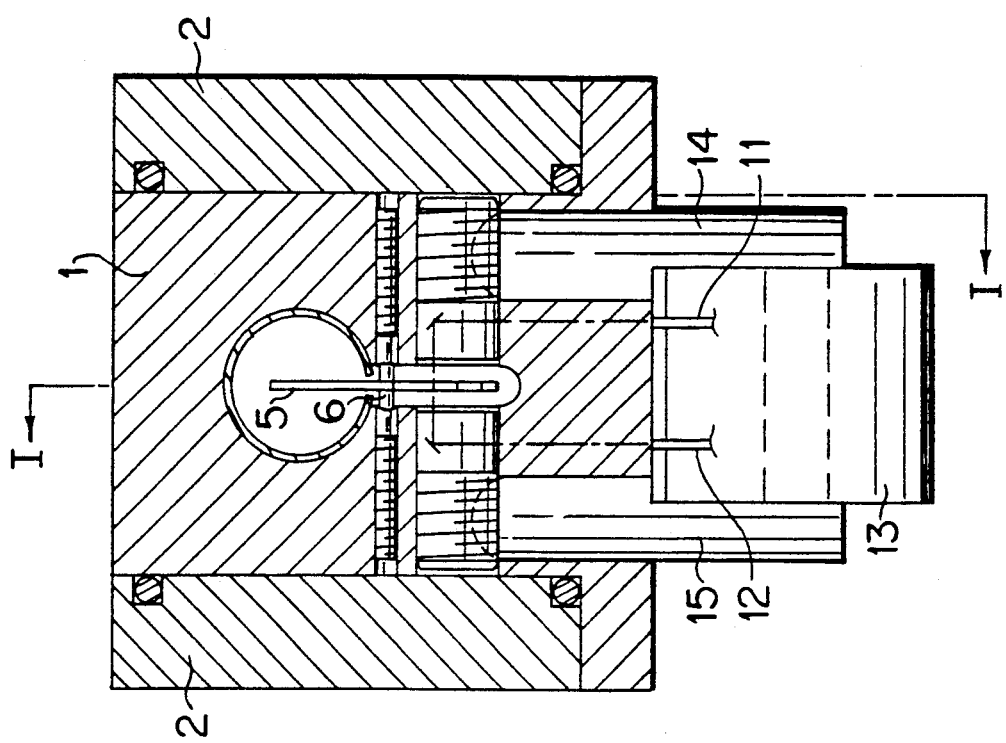
FIG. 2 is a cross-sectional view taken on the line II—II in FIG. 1.
Figure 1:
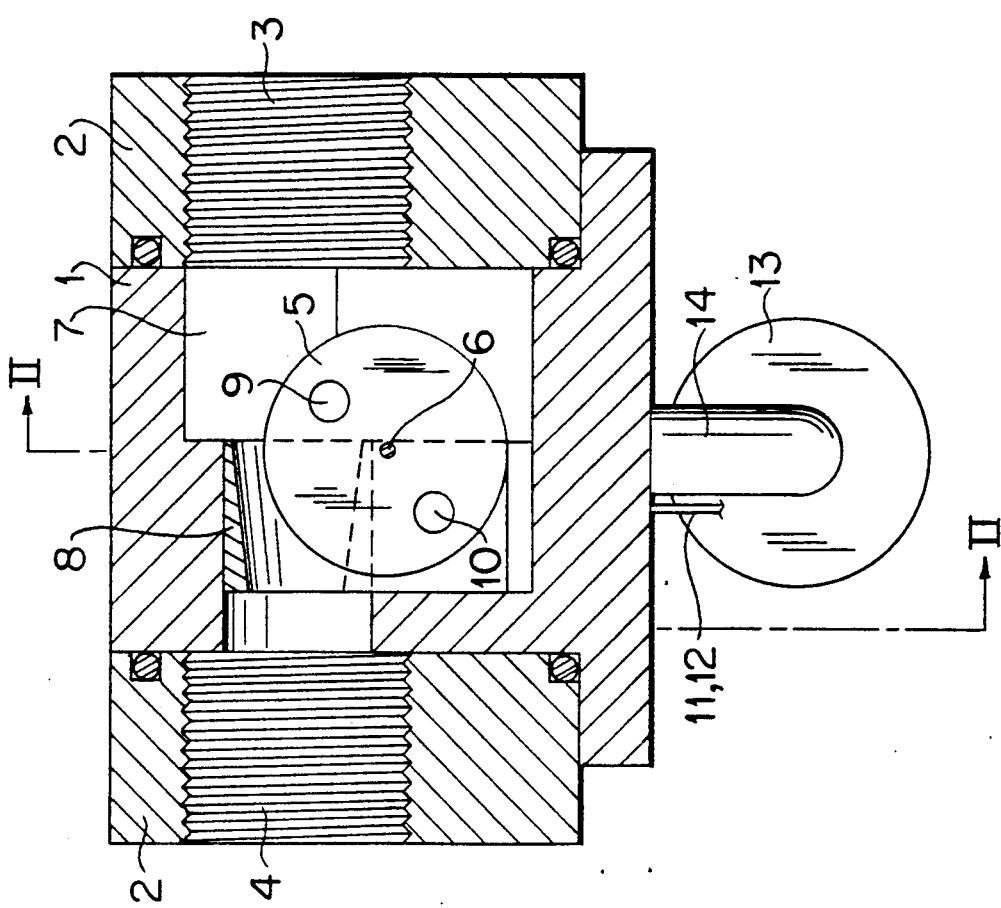
FIG. 1 is a longitudinal sectional view of a first embodiment of a viscosity measuring device in accordance with the invention taken on the line I—I in FIG. 2.

In the embodiment illustrated in FIGS. 1 and 2, the body 1 of the measuring device is incorporated in a passage 2 having an inlet 3 and an outlet 4. The rotor of the device has the form of a circular plate 5 which is journalled symmetrically on a shaft 6 which extends perpendicularly to the longitudinal axis of the passage 2. The plate 5 is mounted in a space 7 in the body 1 which is located asymmetrically to the longitudinal axis of the passage 2. Located at the outlet of the space 7 leading to the outlet 4 of the passage is a flow-throttling nozzle 8. The plate 5 has provided therein two bores 9 and 10 which extend parallel with the axis of the plate 5. These bores are operative to receive light from one light-conductor, e.g., light-conductor 11, and to conduct said light to another light-conductor, e.g., light-conductor 12. This will enable the rotational speed of the plate 5 to be measured on the basis of the time which passes between those time points at which light-conductor 12 receives light from light-conductor 11.

The viscosity meter has a brake device in the form of an eddy-current brake device comprising a coil 13 and two magnetic poles 14 and 15. As an alternative to an electromagnetic brake device, the inventive meter may be provided with a permanent-magnetic brake provided with adjustable magnets, or with a mechanical brake having force applying means.

Figure 3:
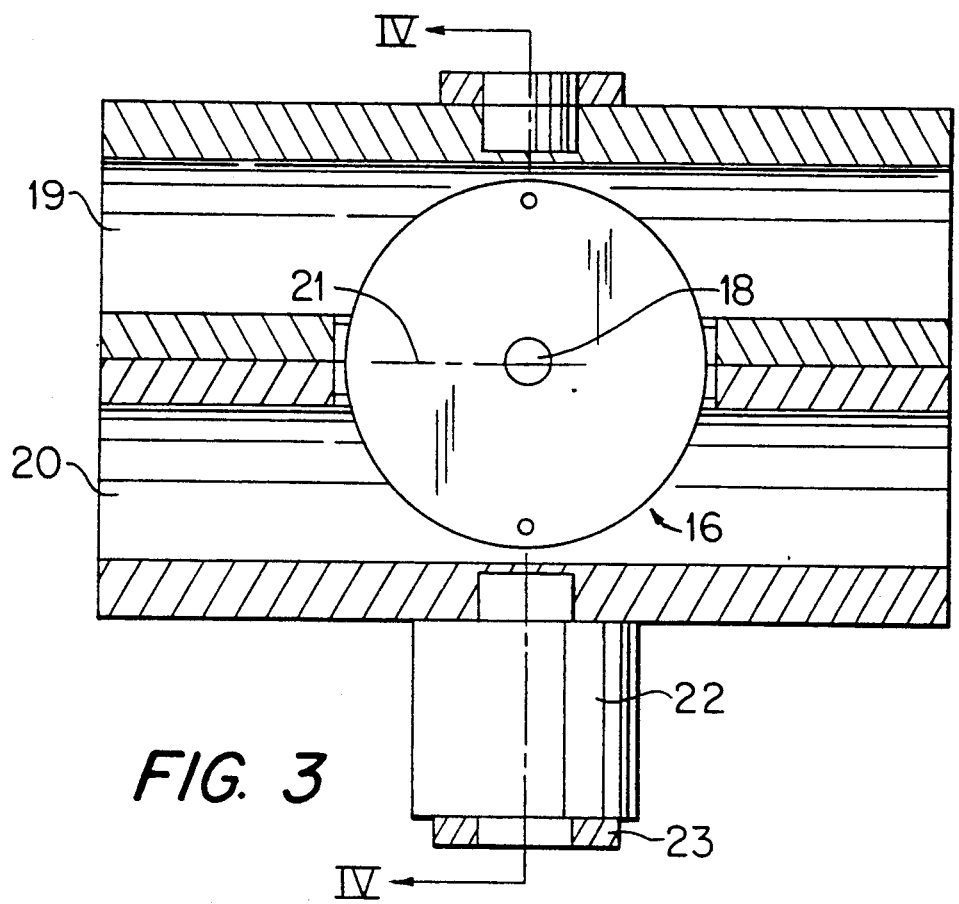
FIG. 3 is a longitudinal sectional view of a second embodiment of a viscosity measuring device in accordance with the inventive device.
Figure 4:
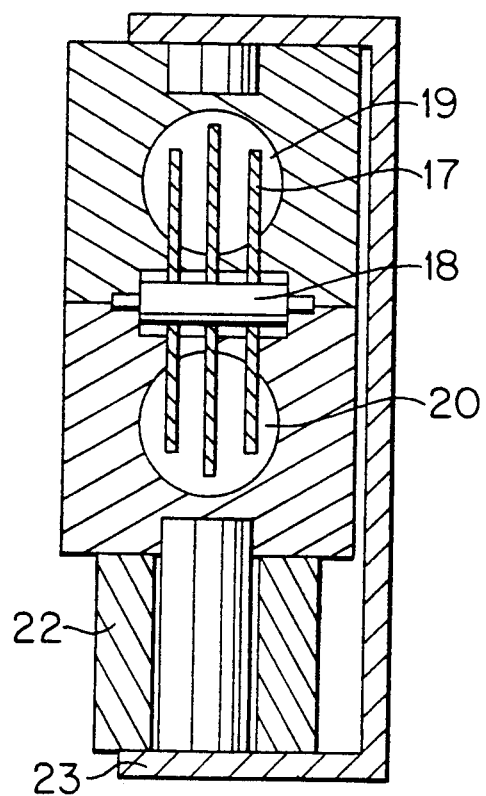
FIG. 4 is a cross-sectional view taken on the line IV—IV in FIG. 3.
Figure 5:
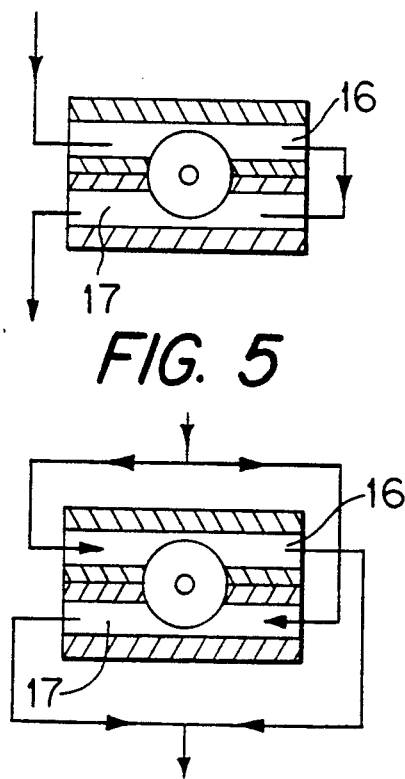
FIGS. 5 and 6 illustrate, in smaller scale, coupling of the device illustrated in FIGS. 3 and 4 in a fluid passage.
Figure 6:
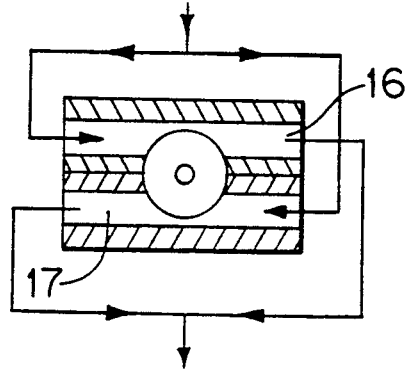

The embodiment of the meter illustrated in FIGS. 3, 4, 5, and 6 includes a rotor 16 which comprises three mutually parallel and circular plates 17 journalled on a common shaft 18. The rotor 16 is mounted so as to lie in two mutually parallel conduits 19, 20 which are the mirror image of one another about an imaginary axis 21 passing through the center of the rotor 16. The rotor journals are fully relieved of the forces exerted by the fluid on the rotor, when the fluid flows in mutually opposite directions through the conduits 19, 20, as illustrated in FIGS. 5 and 6. In the FIG. 5 illustration, conduits 19, 20 are connected in series, whereas in the FIG. 6 illustration the conduits are connected in parallel. The brake device of this embodiment has the form of a hysteresis brake device having a coil 22 and magnetic poles 23.

In accordance with the invention method in the case of the embodiment illustrated in FIGS. 1 and 2, the rotor 4 is connected to an activatable and deactivatable brake device 13, 14, 15, the braking force of which can be adjusted. The braking force exerted by the brake device is adjusted so that the rotor will rotate at a lower speed, to a greater or a lesser extent, than a rotor which is not braked or a rotor whose speed has been retarded with a smaller braking force. Thus, constant rotor speeds are determined and the viscosity of the fluid calculated on the basis of the difference in these rotational speeds.

The inventive measuring device is not limited to the aforedescribed, preferred embodiments, and modifications are possible within the scope of the claims. For instance, the brake device may have the form of a magnetic brake of the eddy-current or hysteresis type, comprising a displaceable permanent magnet and a brake-rotor of ferromagnetic material when the brake device is of the hysteresis kind, and of non-ferromagnetic material when the brake device is of the eddy-current kind. The brake device may also comprise a displaceable, positionally adjustable, permanent magnet and may then be provided with a push rod provided with a knob for manually activating and deactivating the magnetic field.

Other rotors than the rotors illustrated in the drawings are also conceivable, such as a circular cylinder.

Another conceivable type of meter is one in which the brake device comprises electromagnets or permanent magnets provided with displaceable pole shoes.

The magnetic poles may be inserted into a bore provided in the casing, without needing to penetrate the channel wall. This reduces the risk of leakage to insignificant values. A simple construction can be achieved by using a one-sided horseshoe-type magnet which can be pushed in and out.

The device may be constructed so that during a measuring process the rotor will constantly rotate at mutually the same speed when no load is on the rotor, by providing an adjustable constriction or a fixed constriction upstream or downstream of the meter, so as to maintain the prescribed rotor speed. The reduction in rotor speed caused by braking can then be read directly as the viscosity indicated by appropriate graduation of a speed scale.

The measuring means incorporated in the inventive device can be connected to a microprocesser provided with an LCD-display.

The measuring means may include a graduated scale which discloses how close to the rotor the permanent magnet must be brought in order to achieve a given lag in rotor speed.

In the embodiment of FIGS. 7 and 8, rotor 30 is mounted in a body 31 having a U-shaped fluid passage 32 with the rotor positioned at or near the bottom of the U. The fluid passage has a fluid inlet 33 along one leg of the U and a fluid outlet 34 along the other leg of the U and the fluid thus flows in opposite directions through the legs, thus relieving the rotor journals of forces exerted by the fluid on the rotor. The rotor is positioned symmetrically between the legs of the U-shaped passage such that the rotor extends symmetrically into the legs of the U-shaped passage similarly as in the embodiment of FIGS. 3 and 4, and the legs are preferably mutually parallel. Preferably, the rotor is positioned at or near the bottom of the U-shaped passage such that the rotor is in contact with fluid along the full length of the curved bottom portion of the U-shaped flow path. The curved bottom portion 40 of the U-shaped flow path may be semi-circular in section as shown in FIG. 7 in which case it is preferred to mount the rotor such that the rotor and semi-circle are concentric as shown in FIG. 7. Body 31 is preferably made in two portions 35, 36. Rotor 30 is mounted for rotation in slot 37 of body portion 36. Body portion 36, with rotor 30 mounted therein as shown, is then inserted into a cavity 38 in body portion 35 such that rotor 30 is positioned in the device as shown in FIGS. 7 and 8. A sealing gasket 39 is provided between body portions 35 and 36 and the assembly is secured by bolts, not shown, which extend through holes (not shown) in body portion 36 into blind holes 41 in body portion 35. The device is provided with a magnetic brake comprising iron core 42, coil 43, and pole 44. Rotational speed of rotor 30 is conveniently detected by detecting light transmitted from fiber optic element 45, through one or more holes 46 in rotor 30, and through fiber optic element 47 to a detector (not shown).

The fluid flow path in the embodiment depicted in FIGS. 9 and 10 is like that of FIGS. 3 and 4, with cylindrical rotor 50 being disposed between two mutually parallel flow passages 51 and 52 such that the forces on the rotor journals are relieved. In this embodiment, however, the rotor is a circular cylinder. Cylindrical rotor 50 is mounted for rotation about its cylindrical axis which extends substantially at right angles to the longitudinal axis of the flow passages with the rotor axis being located asymmetrically with respect to the longitudinal axis of each of the flow passages. An advantage of the cylindrical rotor is in the manufacturing ease, relative to a thin plate, of mounting the rotor such that it is substantially free of wobble. The body of the device of FIG. 10 is preferably fabricated in three pieces. Main body portion 53 includes flow passage 51 and 52 and a cylindrical aperture 54 extending through body portion 53 transverse to the flow passages for receiving cylindrical rotor 50. Rotor 50 is journalled for rotation in second and third body portions 55, 56 which are also received in aperture 54 and secured therein by suitable means such as bolts (not shown). The device is provided with a magnetic brake comprising iron core 57, coil 58, and poles 59. Rotational speed of the rotor is conveniently detected by a light detection system as described in connection with FIGS. 7 and 8 and not shown in FIGS. 9 and 10.

Although the invention has been described in the foregoing with reference to several embodiments thereof, it will be understood that other embodiments can also be realized within the scope of the invention as defined in the following claims.

What is claimed is:

1. A device for determining the viscosity of a fluid flowing in a closed passage, said device comprising:
    a rotor which, in use of the device, is surrounded by the fluid and the speed of rotation of which is directly dependent on the flow rate of the fluid, said rotor being carried symmetrically by a shaft which extends substantially at right angles to the longitudinal axis of the passage, said rotor shaft being located asymmetrically in relation to the longitudinal axis of said passage so that when fluid flows at constant velocity through the conduit the rotor will rotate at constant velocity, said rotor having the form of circular plate or cylinder;
    brake means for applying a braking force to the rotor, the braking force being sufficient to cause the rotor to rotate at a reduced constant speed in relation to the constant speed of an unbraked rotor or of a rotor braked with a smaller braking force; and
    rotational speed measuring means for measuring the resulting different constant rotational speeds of the rotor, a difference in said constant rotational speeds being representative of the viscosity of the fluid.

2. A device according to claim 1 wherein said brake means comprises an electromagnetic brake comprising a coil and magnetic poles.

3. A device according to claim 1, wherein the rotor lies in mutually parallel passages.

4. A device according to claim 3 wherein said parallel passages are the mirror image of one another around a longitudinal axis passing through the center of the rotor.

5. A device according to claim 1, wherein the rotational speed measuring means comprises light receiver means.

6. A device according to claim 2, wherein said electromagnetic brake is of the eddy-current type.

7. A device according to claim 2, wherein said electromagnetic brake is of the hysteresis type.

8. A device according to claim 1 wherein said rotor comprises a plurality of said circular plates mounted on one and the same shaft.

9. A method of determining the viscosity of a fluid flowing in a closed passage which comprises:
 (a) providing a rotor which is surrounded by the fluid in said passage, the speed of rotation of the rotor being directly dependent on the flow rate of the fluid, the rotor being carried symmetrically by a shaft which extends substantially at right angles to the longitudinal axis of the passage, said rotor shaft being located asymmetrically in relation to the longitudinal axis of said passage so that when a fluid flows at constant velocity through the conduit the rotor will rotate at constant velocity, said rotor having the form of a circular plate or cylinder;
 (b) causing a fluid to flow through said passage at an initial constant velocity to cause the rotor to rotate at an initial constant velocity;
 (c) applying a predetermined braking force to the rotor to cause the rotor to rotate at a constant velocity which is reduced in relation to the initial constant velocity; and
 (d) determining, from the difference between the initial and reduced constant velocities of the rotor, the viscosity of said fluid.

10. A process according to claim 9 wherein the rotor is unbraked during step (b).

11. A process according to claim 9 wherein the rotor is braked during step (b) by a braking force which is less than the braking force applied during step (c).

* * * * *